(12) United States Patent
Wong et al.

(10) Patent No.: US 8,802,975 B2
(45) Date of Patent: Aug. 12, 2014

(54) COMPOUNDS FOR ORGANIC THIN-FILM SOLAR CELLS AND ORGANIC THIN-FILM SOLAR CELLS

(75) Inventors: Ken-Tsung Wong, New Taipei (TW); Hao-Wu Lin, Zhubei (TW); Li-Yen Lin, Wujie Township (TW); Francis Lin, New Taipei (TW); Yi-Hong Chen, New Taipei (TW); Shi-Wen Chiu, Taichung (TW)

(73) Assignees: Ken-Tsung Wong (TW); Hao-Wu Lin (TW)

( * ) Notice: Subject to any disclaimer, the term of this patent is extended or adjusted under 35 U.S.C. 154(b) by 208 days.

(21) Appl. No.: 13/342,331

(22) Filed: Jan. 3, 2012

(65) Prior Publication Data

US 2013/0019949 A1 Jan. 24, 2013

(30) Foreign Application Priority Data

Jul. 22, 2011 (TW) .............................. 100126035 A

(51) Int. Cl.
*C07D 285/14* (2006.01)
*C07D 409/04* (2006.01)
*C07D 417/04* (2006.01)
*H01L 51/00* (2006.01)
*H01L 51/42* (2006.01)

(52) U.S. Cl.
CPC .......... *H01L 51/0064* (2013.01); *C07D 285/14* (2013.01); *H01L 51/4253* (2013.01); *H01L 51/0046* (2013.01); *C07D 417/04* (2013.01); *Y02E 10/549* (2013.01); *C07D 409/04* (2013.01)
USPC ........... 136/263; 544/342; 544/347; 544/333; 548/126

(58) Field of Classification Search
CPC .. C07D 285/14; C07D 409/04; C07D 417/04; H01L 51/4253; Y02E 10/549
USPC ............ 136/263; 544/342, 347, 333; 548/126
See application file for complete search history.

(56) References Cited

U.S. PATENT DOCUMENTS

2010/0168444 A1 * 7/2010 Chen et al. ...................... 549/41

OTHER PUBLICATIONS

Lin et al. (J. Am. Chem. Soc. 2011, 133, 15822-15825).*
Lin et al. (J. Mater. Chem., 2011, 21, 5950-published on Mar. 8, 2011).*
Qin et al. (Adv. Mater. 2009, 21, 2993-2996).*
Lin et al. (Chem. Commun., 2011, 47, 7872-7874-published on May 31, 2011).*
Pratt, Derek A. "Substituent Effects on the Bond Dissociation Enthalpies of Aromatic Amines"; J. Am. Chem. Soc. 2002, 124, 11085-11092.
Nakayama, Juzo "Synthesis of Highly Congested BI and Terthiophenes: 3,4,3',4'-Tetra-tert-Butylbithiophene and 3',4'-Diter-Butyl-2,2':5,2" Terthiophene"; Heterocycles vol. 44, No. 1, 1997; 6 pages.
Tkachov, Roman "Influence of Alkyl Substitution Pattern on Reactivity of Thiophene-Based Monomers in Kumada Catalyst-Transfer Polycondensation"; Macromolecules 2011, 44, 2006-2015.
Locke, Jonas R. "Syntheses of Gradient π-Conjugated Copolymers of Thiophene"; Macromolecules 2010, 43, 8709-8710.
El-Shehawy, Ashraf A. A selective and direct synthesis of 2-bromo-4-alkylthiophenes: Convenient and straightforward approaches for the synthesis of head-to-tail (HT) and tail-to-tail (TT) dihexyl-2,20-bithiophenes; Tetrahedron Letters 51 (2010) 4526-4529.
Zhang, Cheng "Design, Synthesis, Characterization, and Modeling of a Series of S,S-Dioxothienylenevinylene-Based Conjugated Polymers with Evolving Frontier Orbitals"; Macromolecules 2009, 42, 663-670.
Marterer, Wolfgang "The Nitration of 8-Methylquinoxalines in Mixed Acid"; Organic Process Research & Development 2003, 7, 318-323.
N. P. Xekoukoulotakis "Synthesis of quinoxalines by cyclization of a-arylimino oximes of a-dicarbonyl compounds"; Tetrahedron Letters 41 (2000) 10299-10302.

* cited by examiner

*Primary Examiner* — Kristin Vajda
*Assistant Examiner* — Valerie Rodriguez-Garcia
(74) *Attorney, Agent, or Firm* — Schmeiser, Olsen & Watts LLP

(57) ABSTRACT

Provided are compounds with a donor moiety, a first acceptor moiety and a second acceptor moiety, as shown by Formula (I):

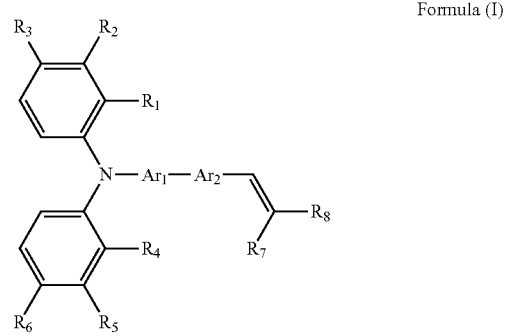

Formula (I)

With the unique molecular design, compounds of Formula (I) can provide a desirable power conversion efficiency. Moreover, this invention also provides organic thin-film solar cells comprising the above-mentioned compounds.

10 Claims, No Drawings

COMPOUNDS FOR ORGANIC THIN-FILM SOLAR CELLS AND ORGANIC THIN-FILM SOLAR CELLS

CROSS-REFERENCE TO RELATED APPLICATION

This non-provisional application claims priority under 35 U.S.C. §119(a) on Patent Application No(s). 100126035 filed in Taiwan, R.O.C. on Jul. 22, 2011, the entire contents of which are hereby incorporated by reference.

FIELD OF TECHNOLOGY

The present invention relates to compounds for solar cells and more particularly to compounds for organic thin-film solar cells, said compounds containing an electron-donating moiety, a first electron-accepting moiety and a second electron-accepting moiety.

BACKGROUND

Due to the over use of petrochemical resources, the living environment of human beings has been getting worse in recent years. To prevent energy depletion problems, more and more people are devoting themselves to the research of solar power generation.

Among various existing solar cell technologies, crystalline silicon-based solar cells and semiconductor-based solar cells provide higher photoelectric conversion efficiencies; however, they are not widely used because of high manufacturing costs.

In contrast, solar cells fabricated by organic materials have gained considerable research interest owing to their prominent merits such as low cost, light weight, mechanical flexibility and feasibility of large area fabrication with relatively simple processes.

Common organic solar cells include dye-sensitized solar cells, polymer organic solar cells, small-molecule organic solar cells, and organic/inorganic hybrid solar cells.

Classified according to their electron donors, small-molecule organic solar cells can be roughly divided into two categories. The first one uses an acceptor-donor-acceptor (A-D-A) molecular architecture, wherein the donor moiety can be for example oligothiophenes of different unit number, and the acceptor moiety can be for example dicyanovinylene. The second category uses a donor-acceptor (D-A) system, wherein the useful donor moiety can be for example arylamines, and the acceptor moiety can be for example dicyanovinylene.

Because the aforesaid two types of small-molecules, when applied to the manufacture of solar cells practically, fail to provide a desirable photoelectric conversion efficiency, there is a need to propose a novel molecular design concept which can be used as the foundation for the development of solar cells.

SUMMARY

It is the primary object of this invention to provide novel compounds applicable to small-molecule organic solar cells or solid state organic thin-film solar cells, as represent by formula (I):

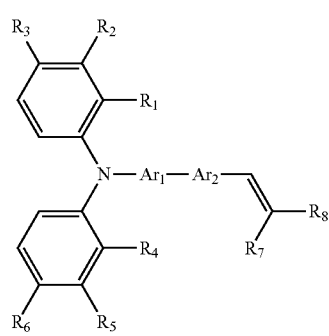

Formula (I)

wherein $R_1$ to $R_6$ are independently selected from H, $C_1$-$C_6$ alkyl group, $C_1$-$C_6$ ether group, and amino group substituted by $C_1$-$C_6$ alkyl group;

$Ar_1$ is selected from

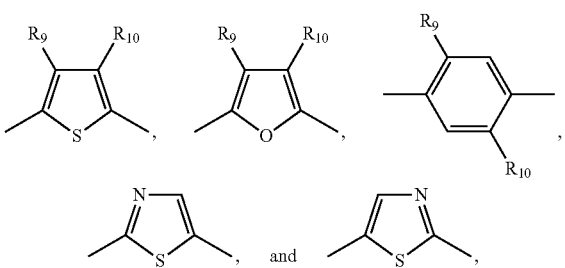

wherein $R_9$ and $R_{10}$ are independently selected from H, F, $C_1$-$C_6$ alkyl group, and $C_1$-$C_6$ ether group;

$Ar_2$ is selected from

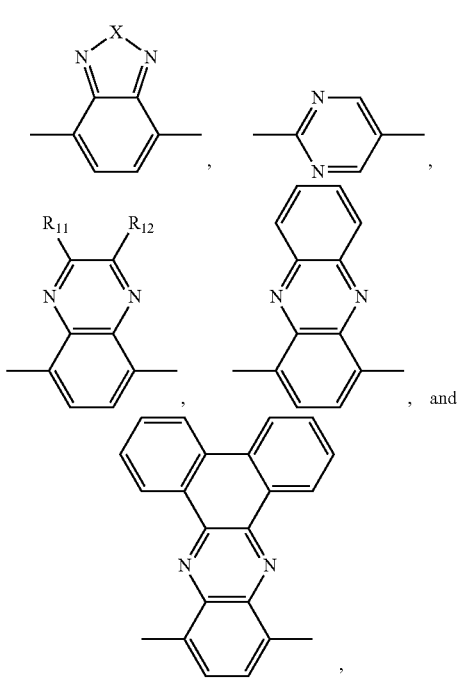

wherein X is O, S, or Se, and $R_{11}$ and $R_{12}$ are independently selected from H, $C_1$-$C_6$ alkyl group, cyano group, and phenyl group; and $R_7$ and $R_8$ are independently selected from cyano group, nitro group, and $C_1$-$C_8$ ester group of carboxylic acid.

It is another object of the present invention to provide organic thin-film solar cells comprising a first electrode, a hole transporting layer, an active layer, an electron transporting layer and a second electrode which are sequentially stacked, wherein the active layer comprises a compound represented by Formula (I) shown above.

DETAILED DESCRIPTION

The present invention will become more readily apparent to those ordinarily skilled in the art after reviewing the following detailed description. In addition, to the extent relevant to describing, making or using the invention as claimed, all the references disclosed herein are hereby incorporated herein.

A part of this invention provides a compound which can be used in the active layer of a solar cell, as shown by Formula (I)

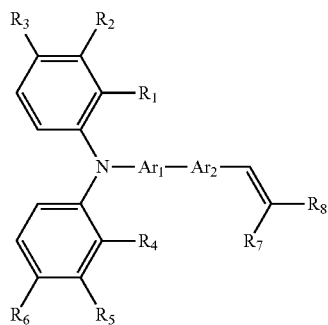

Formula (I)

wherein $R_1$ to $R_6$ and $R_7$ and $R_8$ each represents the same or different substituent, as defined below, and $Ar_1$ and $Ar_2$ each represents an aryl ring described below. Thus, this invention provides an organic dye with low energy gap which is applicable to small-molecule organic solar cells or solid state organic thin-film solar cells.

In the compound represented by Formula (I), the two benzene rings can be unsubstituted or substituted by $R_1$ to $R_6$ at ortho-, meta- and/or para-positions, and $R_1$ to $R_6$ are independently selected from H, which means no substitution occurs, $C_1$-$C_6$ alkyl group, $C_1$-$C_6$ ether group, and amino group substituted by $C_1$-$C_6$ alkyl group. In one embodiment, $R_1$ to $R_6$ are independently selected from H, $C_1$-$C_3$ alkyl group, $C_1$-$C_3$ ether group, and amino group substituted by $C_1$-$C_3$ alkyl group. Preferably, $R_1$ to $R_6$ are independently selected from H and $C_1$-$C_6$ alkyl group, such as methyl group, ethyl group, propyl group, isopropyl group, butyl group, tert-butyl group, isobutyl group, pentyl group, and hexyl group.

$Ar_1$ may be substituted or unsubstituted thiophene, furan, benzene or thiazole. Particularly, $Ar_1$ may be substituted by, for example, F, $C_1$-$C_6$ alkyl group, or $C_1$-$C_6$ ether group and preferably by F, $C_1$-$C_3$ alkyl group, or $C_1$-$C_3$ ether group. In one embodiment, $Ar_1$ is unsubstituted or fluoro-substituted thiophene, furan, benzene or thiazole.

Thus, a portion of the structure of Formula (I), as shown below, represents a strong electron-donating moiety:

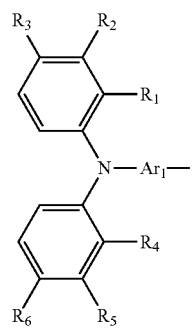

In the compound of Formula (I), $Ar_2$ is selected from

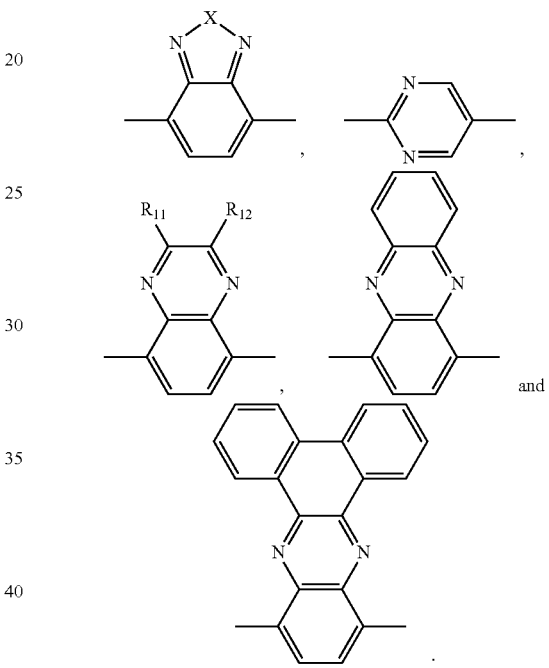

and

X may be O, S, or Se, and $R_{11}$ and $R_{12}$ are independently selected from H, $C_1$-$C_6$ alkyl group, cyano group, and phenyl group. In one embodiment, $Ar_2$ is 2,1,3-benzothiadiazole or pyrimidine. Therefore, $Ar_2$ represents a first electron-accepting moiety of the structure of Formula (I).

In the compound of Formula (I), $R_7$ and $R_8$ are independently selected from cyano group, nitro group, and $C_1$-$C_8$ ester group of carboxylic acid, thereby introducing dicyanovinylene, dinitrovinylene or diester vinylene to the molecular structure as a second electron-accepting moiety.

Accordingly, the electron-donating moiety, the first electron-accepting moiety and the second electron-accepting moiety of Formula (I) form a novel donor-acceptor-acceptor (DAA) architecture for an organic photovoltaic material capable of using the radiation of UV-visible and/or near infrared region in the solar spectrum and providing a desirable energy conversion efficiency.

Another part of this invention provides an organic thin-film solar cell comprising a first electrode, a hole transporting layer, an active layer, an electron transporting layer and a second electrode which are sequentially stacked, wherein the active layer comprises the compound represented by Formula (I) above.

The first electrode can be any transparent conductive oxide, including but not limited to indium tin oxide and indium zinc oxide, and the first electrode is generally formed on a transparent substrate such as glass. In addition, silver, aluminum and PEDOT:PSS can also be used as the first electrode, but not limited thereto.

The hole transporting layer is disposed between the first electrode and the active layer and comprises hole transporting material, which may be but not limited to HAT(CN)$_6$, MoO$_3$, PEDOT:PSS, PEDOT:PSS/HAT(CN)$_6$, or PEDOT:PSS/MoO$_3$.

The active layer is disposed between the hole transporting layer and the electron transporting layer and includes organic photovoltaic material, such as a mixture of the compound of Formula (I) as the electron donor and an electron acceptor. Useful electron acceptor may be, but not limited to, fullerene, such as C$_{60}$, C$_{70}$ or derivatives thereof, and a small-molecule electron acceptor such as PTCBI or PTCDA.

It is understood by a person skilled in the art that the term "active layer" has various forms and is not limited to a single layer structure. For example, the active layer may be a planar-mixed heterojunction (PMHJ), which comprises an electron donor layer, an electron acceptor layer and a donor/acceptor mixture layer disposed therebetween.

The electron transporting layer is disposed between the active layer and the second electrode and comprises electron transporting material, which includes without limitation 2,9-dimethyl-4,7-diphenyl-1,10-phenanthroline (BCP), Bphen, TPBi, TyPMPB, PTCBI, NTCDA, C$_{60}$, C$_{70}$, PTCDA, ZnO, or TiO$_2$.

The second electrode is formed on the electron transporting layer as a cathode. Commonly used second electrode includes silver, for example, but other material, such as Ca, Cs, CsF, Li, LiF, Mg, or Al can be used, too.

In addition to a stand-alone photoelectric conversion device, the organic thin-film solar cell can also be fabricated as a tandem structure, in which different subunits can use the same or different active layer material.

To further illustrate the compounds and solar cells of this invention, several examples and embodiments are cited with synthesis schemes thereof described in a way to enable a person skilled in the art to make and use this invention. Most reagents were commercially available and used without purification. Solvents for chemical synthesis were purified by distillation, and all chemical reactions were carried out under an argon or nitrogen atmosphere.

Chemical Synthesis Scheme I

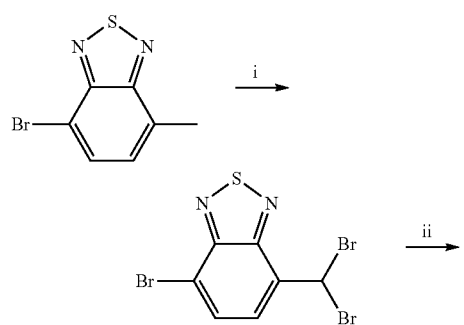

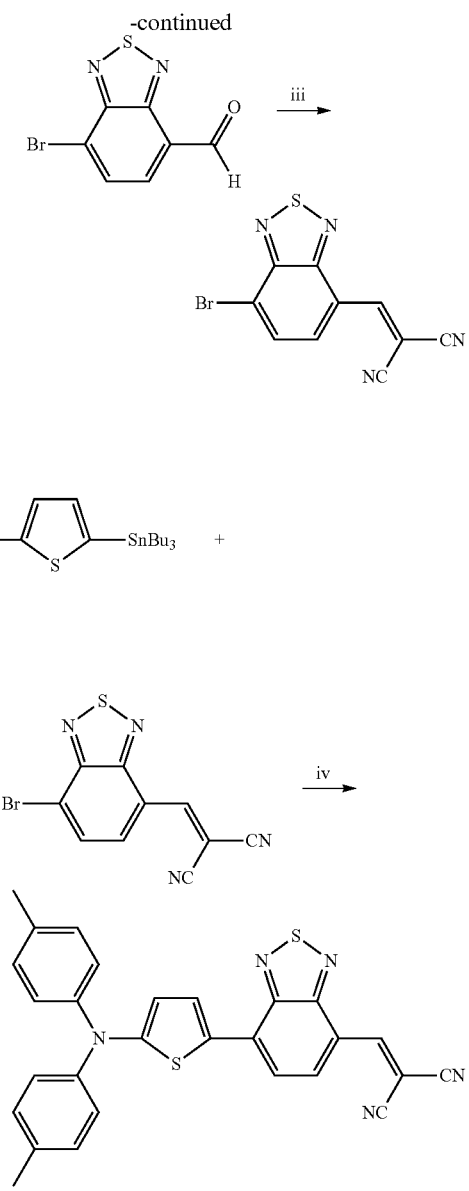

The reaction condition of each step is as follows:
(i) N-bromosuccinimide (NBS), azobisisobutyronitrile (AIBN), chlorobenzene, 80° C.;
(ii) AgNO$_3$, H$_2$O/MeCN, reflux;
(iii) malononitrile, Al$_2$O$_3$, toluene, 70° C.;
(iv) [PdCl$_2$(PPh$_3$)$_2$], toluene, 110° C.

Synthesis of Compound A—4-Bromo-7-dibromomethyl-2,1,3-benzothiadiazole

A mixture of 4-bromo-7-methyl-2,1,3-benzothiadiazole (45.82 g, 200 mmol), AIBN (6.57 g, 40 mmol), and NBS (106.2 g, 600 mmol) in chlorobenzene (400 mL) was stirred and heated at 80° C. for 4 hours. After cooling to room temperature, the reaction mixture was filtered to remove the solid succinimide, and then the filtrate was washed with water and brine, dried over anhydrous MgSO$_4$, and filtered. The solvent of the filtrate was removed by rotary evaporation, and the crude product was purified by column chromatography on silica gel with CH$_2$Cl$_2$/hexane (v/v, 1:3) as eluent to afford Compound A as a white solid (56.1 g, 83%). The analytical data obtained from Compound A are listed below. M.p. 119-120° C.; IR (KBr) v 3001, 2922, 1524, 1481, 1315, 1274, 1185, 1097, 937, 880 cm$^{-1}$; $^1$H NMR (CDCl$_3$, 400 MHz) δ 7.97-7.90 (m, 2H), 7.40 (s, 1H); $^{13}$C NMR (CDCl$_3$, 100 MHz) δ 152.8, 149.6, 133.4, 131.8, 129.4, 115.8, 33.9; HRMS (m/z, FAB$^+$) Calcd. for C$_7$H$_3$$^{79}$Br$_3$N$_2$S 383.7567. found 383.7542, Calcd. for C$_7$H$_3$$^{79}$Br$_2$$^{81}$Br$_1$N$_2$S 385.7547. found 385.7553, Calcd. for C$_7$H$_3$$^{79}$Br$_1$$^{81}$Br$_2$N$_2$S 387.7526. found 387.7524, Calcd. for C$_7$H$_3$$^{81}$Br$_3$N$_2$S 389.7506. found 389.7536.

Synthesis of Compound B—7-Bromo-2,1,3-benzothiadiazole-4-carbaldehyde

To a stirring solution of Compound A (260 mg, 0.67 mmol) in acetonitrile (8 mL) was added silver nitrate aqueous solution (285 mg, 1.68 mmol, water 1.7 mL) and then heated to reflux for 2 hours. After cooling to room temperature, the reaction mixture was filtered to remove the AgBr precipitate, and the filtrate was then extracted with CH$_2$Cl$_2$. The combined extracts were washed with brine, dried over anhydrous MgSO$_4$, and filtered. The solvent of the extracts was removed by rotary evaporation to afford Compound B as a white solid (147 mg, 92%). The analytical data obtained from Compound B are listed below. M.p. 185-186° C.; IR (KBr) v 3078, 3021, 2835, 2728, 1702, 1526, 1268, 1102, 937, 879 cm$^{-1}$; $^1$H NMR (CDCl$_3$, 400 MHz) δ 10.71 (s, 1H), 8.09-8.03 (m, 2H); $^{13}$C NMR (CDCl$_3$, 100 MHz) δ 188.0, 153.8, 152.1, 131.9, 131.5, 126.7, 121.7; HRMS (m/z, FAB$^+$) Calcd. for C$_7$H$_3$$^{79}$BrN$_2$OS 241.9149. found 241.9149, Calcd. for C$_7$H$_3$$^{81}$BrN$_2$OS 243.9129. found 243.9137.

Synthesis of Compound C—4-Bromo-7-dicyanovinyl-2,1,3-benzothiadiazole

A mixture of Compound B (150 mg, 0.62 mmol), malononitrile (82 mg, 1.24 mmol), and basic aluminum oxide (310 mg) in dry toluene (7 mL) was stirred and heated at 70° C. for 2 hours. After the reaction mixture was cooled to room temperature, the basic aluminum oxide residue was removed by filtration and thoroughly washed with toluene. The solvent of the filtrate was removed by rotary evaporation, and the crude product was purified by column chromatography on silica gel with CH$_2$Cl$_2$/hexane (v/v, 1:1) as eluent to afford Compound C as a yellow solid (120 mg, 67%). The analytical data obtained from Compound C are listed below. M.p. 179-180° C.; IR (KBr) v 3097, 3032, 2229, 1573, 1517, 1380, 1126, 1044, 933, 884 cm$^{-1}$; $^1$H NMR (CDCl$_3$, 400 MHz) δ 8.73 (s, 1H), 8.53 (d, J=7.6 Hz, 1H), 8.05 (d, J=7.6 Hz, 1H); $^{13}$C NMR (CDCl$_3$, 100 MHz) δ 153.0, 152.5, 152.2, 132.0, 130.0, 123.0, 121.8, 113.1, 112.3, 85.2; HRMS (m/z, FAB$^+$) Calcd. for C$_{10}$H$_3$$^{79}$BrN$_4$S 289.9262. found 289.9263, Calcd. for C$_{10}$H$_3$$^{81}$BrN$_4$S 291.9241. found 291.9237.

Synthesis of Compound D—2-{[7-(5-N,N-ditolylaminothiophen-2-yl)-2,1,3-benzothiadiazol-4-yl]methylene}malononitrile A mixture of Compound C (1.46 g, 5 mmol), 5-(N,N-ditolylamino)-2-(tri-n-butylstannyl)thiophene (3.55 g, 6.25 mmol), and PdCl$_2$(PPh$_3$)$_2$ (175 mg, 0.25 mmol) in dry toluene (25 mL) was stirred and heated at 110° C. under argon for 2 hours. After the reaction mixture was cooled to room temperature, the solvent was removed by rotary evaporation, and the crude product was purified by column chromatography on silica gel with CH$_2$Cl$_2$/hexane (v/v, 1:1) as eluent to afford Compound D as a black solid (1.34 g, 55%). The analytical data obtained from Compound D are listed below. M.p. 234° C. (DSC); IR (KBr) v 3033, 2917, 2217, 1566, 1454, 1329, 1265, 1153, 1062, 921, 827 cm$^{-1}$; $^1$H NMR (CDCl$_3$, 400 MHz) δ 8.66 (s, 1H), 8.60 (d, J=8.0 Hz, 1H), 8.22 (d, J=4.4 Hz, 1H), 7.57 (d, J=8.0 Hz, 1H), 7.22-7.17 (m, 8H), 6.50 (d, J=4.4 Hz, 1H), 2.39 (s, 6H); $^{13}$C NMR (CDCl$_3$, 100 MHz) δ 161.0, 154.6, 151.5, 150.6, 143.8, 135.5, 134.0, 133.2, 130.8, 130.2, 126.0, 124.9, 120.9, 118.9, 114.6, 114.3, 113.8, 78.5, 21.1; HRMS (m/z, FAB$^+$) Calcd. for C$_{28}$H$_{19}$N$_5$S$_2$ 489.1082. found 489.1083.

Synthesis of 2-{[7-(5-N,N-diphenylaminothiophen-2-yl)-2,1,3-benzothiadiazol-4-yl]methylene}malononitrile (Compound E), 2-{[7-(4-N,N-diphenylaminophenyl)-2,1,3-benzothiadiazol-4-yl]methylene}malononitrile (Compound F), and 2-{[7-(4-N,N-ditolylaminophenyl)-2,1,3-benzothiadiazol-4-yl]methylene}malononitrile (Compound G)

Compound E

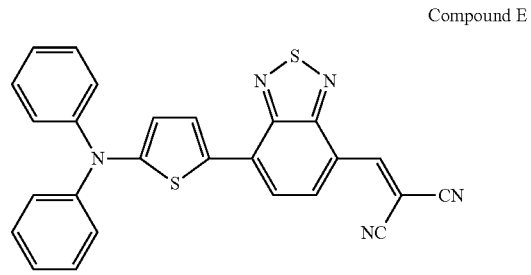

Compound F

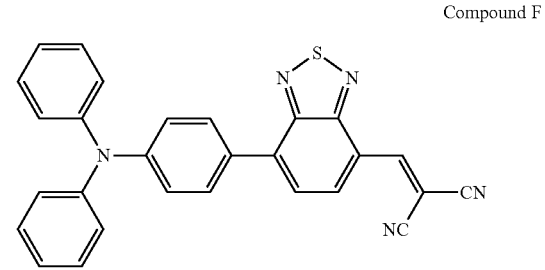

Compound G

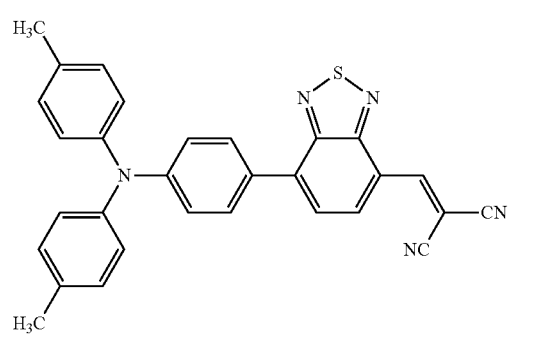

A mixture of Compound C (1.46 g, 5 mmol), 5-(N,N-diphenylamino)-2-(tri-n-butylstannyl)thiophene (3.38 g, 6.25 mmol), and PdCl$_2$(PPh$_3$)$_2$ (175 mg, 0.25 mmol) in dry toluene (25 mL) was stirred and heated at 110° C. under argon for 2 hours. After the reaction mixture was cooled to room temperature, the solvent was removed by rotary evaporation, and the crude product was purified by column chromatography on silica gel with CH$_2$Cl$_2$/hexane (v/v, 1:1) as eluent to afford Compound E as a black solid (1.50 g, 65%).

N,N-Diphenyl-4-(tri-n-butylstannyl)aniline (3.34 g, 6.25 mmol) was used in place of 5-(N,N-diphenylamino)-2-(tri-n- butylstannyl)thiophene above in the reaction, which was stirred and heated for 6 hours, and Compound F as a black solid (1.12 g, 49%) was obtained in a similar way.

N,N-Ditolyl-4-(tri-n-butylstannyl)aniline (3.52 g, 6.25 mmol) was used in place of N,N-Diphenyl-4-(tri-n-butylstannyl)aniline above in the reaction, which was stirred and heated for 5 hours, and Compound G as a black solid (1.64 g, 68%) was obtained in a similar way using $CH_2Cl_2$/hexane (v/v, 4:3) as eluent.

Synthesis of 2-{[7-(2-fluoro-4-N,N-ditolylaminophenyl)-2,1,3-benzothiadiazol-4-yl]methylene}malononitrile (Compound H) and 2-{[7-(3-fluoro-4-N,N-ditolylaminophenyl)-2,1,3-benzothiadiazol-4-yl]methylene}malononitrile (Compound I)

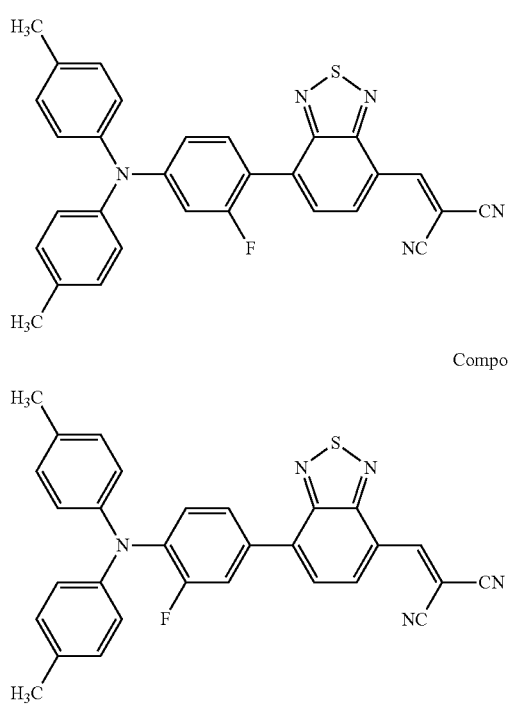

A mixture of Compound C (2.43 g, 8.33 mmol), N,N-ditolyl-4-(tri-n-butylstannyl)-3-fluoroaniline (5.80 g, 10.0 mmol), and $PdCl_2(PPh_3)_2$ (295 mg, 0.42 mmol) in dry toluene (40 mL) was stirred and heated at 110° C. under argon for 4 hours. After the reaction mixture was cooled to room temperature, the solvent was removed by rotary evaporation, and the crude product was purified by column chromatography on silica gel with $CH_2Cl_2$/hexane (v/v, 1:1) as eluent to afford Compound H as a black solid (2.59, 62%).

N,N-Ditolyl-4-(tri-n-butylstannyl)-2-fluoroaniline (5.80 g, 10.0 mmol) was used in place of N,N-ditolyl-4-(tri-n-butylstannyl)-3-fluoroaniline above in the reaction, and Compound I as a black solid (2.58 g, 62%) was obtained in a similar way using $CH_2Cl_2$/hexane (v/v, 4:3) as eluent.

Chemical Synthesis Scheme II

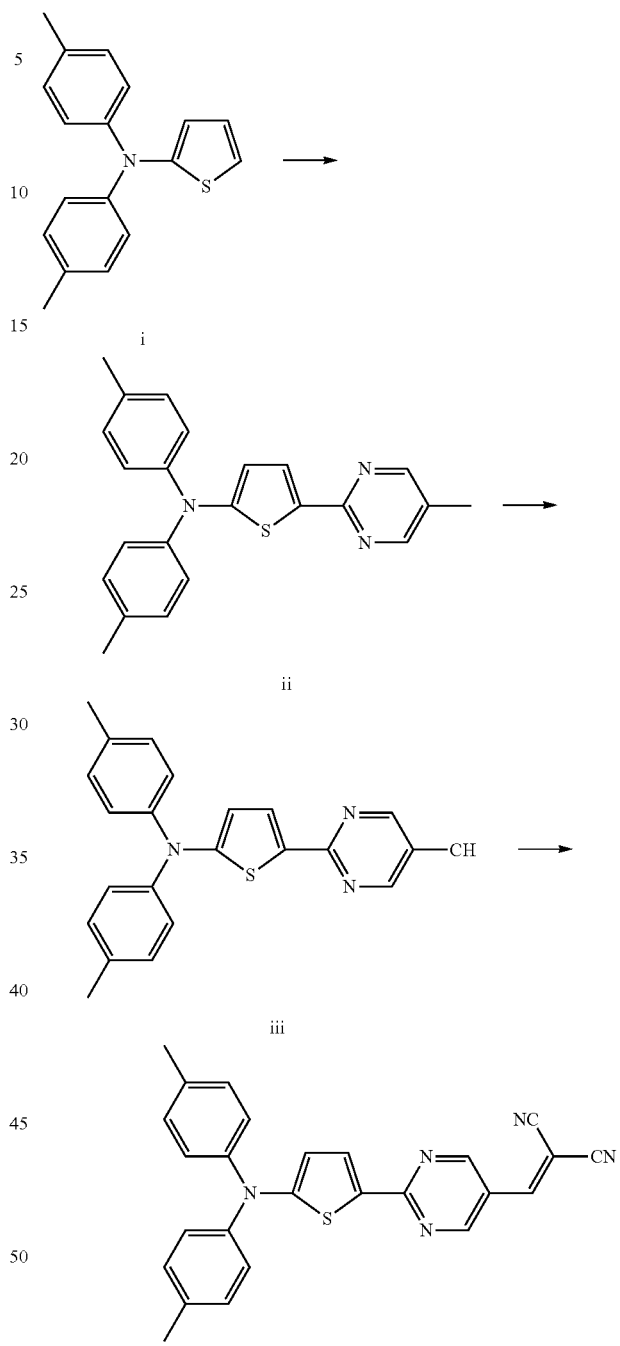

The reaction condition of each step is as follows:
(i) n-Butyllithium, THF, −78° C., then $ZnCl_2$, −35° C., then 5-bromo-2-iodopyrimidine, [Pd $(PPh_3)_4$], reflux;
(ii) n-Butyllithium, THF, −100° C., then ethyl formate, −100° C.;
(iii) malononitrile, $Al_2O_3$, toluene, 70° C.

Synthesis of Compound J—[5-(5-bromo-pyrimidin-2-yl)-thiophen-2-yl]-N,N-di(p-tolyl)amine To a stirring solution of 2-[N,N-di(p-tolyl)amino]thiophene (8.31 g, 30 mmol) in anhydrous THF (90 mL) was dropwise added n-BuLi (1.6 M, 19.69 mL, 31.5 mmol) at −78° C. under argon atmosphere. The reaction mixture was warmed to −35° C. and stirred for 15 min. ZnCl$_2$ (33 mL of 1 M solution in anhydrous THF, 33 mmol) was then added to the reaction mixture in one portion, after which the reaction mixture was warmed to room temperature and stirred for 30 min. To the above resulting zinc reagent was added 5-bromo-2-iodopyrimidine (8.55 g, 30 mmol), Pd(PPh$_3$)$_4$ (1.73 g, 1.5 mmol), and anhydrous THF (120 mL). The whole mixture was heated to reflux under argon atmosphere for 2 hours. After cooling to room temperature, the reaction mixture was poured into water and extracted with ethyl acetate, and the combined extracts were washed with brine, dried over anhydrous MgSO$_4$ and filtered. The solvent was removed by rotary evaporation, and the crude product was purified by column chromatography on silica gel with CH$_2$Cl$_2$/hexane (v/v, 1:2) as eluent to afford Compound J as a yellow solid (10.84 g, 83%). The analytical data obtained from Compound J are listed below. M.p. 173-174° C.; IR (KBr) v 3028, 2916, 1605, 1551, 1374, 1119, 1056, 928 cm$^{-1}$; $^1$H NMR (CDCl$_3$, 400 MHz) δ 8.55 (s, 2H), 7.71 (d, J=4.4 Hz, 1H), 7.16-7.10 (m, 8H), 6.43 (d, J=4.4 Hz, 1H), 2.34 (s, 6H); $^{13}$C NMR (CDCl$_3$, 100 MHz) δ 159.5, 158.9, 157.2, 144.4, 134.3, 130.0, 129.8, 128.9, 124.4, 114.7, 114.5, 21.0; HRMS (m/z, FAB$^+$) Calcd. for C$_{22}$H$_{18}$$^{79}$BrN$_3$S 435.0405. found 435.0411. Calcd. for C$_{22}$H$_{18}$$^{81}$BrN$_3$S 437.0384. found 437.0391.

Synthesis of Compound K—2-[5-N,N-di(p-tolyl) aminothiophen-2-yl]-pyrimidine-5-carbaldehyde To a stirring solution of Compound J (8.73 g, 20 mmol) in 350 mL anhydrous THF was dropwise added n-BuLi (1.6 M, 13.13 mL, 21 mmol) at −100° C. under argon atmosphere. The resulting solution was stirred for 30 min, after which dry ethyl formate (16.15 mL, 200 mmol) was added dropwise over 5 min. After stirring for 30 min, the reaction was quenched with 1.5 M HCl in THF solution (15 mL, 22.5 mmol). The cold bath was removed, and the reaction mixture was stirred for 2 hours. The THF was removed by rotary evaporation and the reaction mixture was extracted with chloroform; the combined extracts were washed with brine, dried over anhydrous MgSO$_4$ and filtered. The solvent was removed by rotary evaporation, and the crude product was purified by column chromatography on silica gel with CH$_2$Cl$_2$ as eluent to afford Compound K as an orange solid (3.27 g, 42%). The analytical data obtained from Compound K are listed below. M.p. 176-177° C.; IR (KBr) v 3027, 2918, 2825, 2719, 1694, 1593, 1547, 1209, 1071 cm$^{-1}$; $^1$H NMR (CDCl$_3$, 400 MHz) δ 9.92 (s, 1H), 8.88 (s, 2H), 7.88 (d, J=4.4 Hz, 1H), 7.20-7.14 (m, 8H), 6.40 (d, J=4.4 Hz, 1H), 2.36 (s, 6H); $^{13}$C NMR (CDCl$_3$, 100 MHz) δ 187.9, 164.1, 162.7, 158.4, 143.7, 135.4, 133.4, 130.2, 127.3, 125.1, 124.1, 113.1, 21.1; HRMS (m/z, FAB$^+$) Calcd. for C$_{23}$H$_{19}$N$_3$OS 385.1249. found 385.1252.

Synthesis of Compound L—2-{[2-(5-N,N-di(p-tolyl) aminothiophen-2-yl)-pyrimidin-5-yl] methylene}malononitrile A mixture of Compound K (1.54 g, 4.00 mmol), malononitrile (528 mg, 8.00 mmol), and basic aluminum oxide (2.00 g) in dry toluene (60 mL) was stirred and heated at 70° C. for 1 hour. After the reaction mixture was cooling to room temperature, the basic aluminum oxide residue was removed by filtration and thoroughly washed with toluene. Solvent of the filtrate was removed by rotary evaporation, and the crude product was purified by column chromatography on silica gel with CH$_2$Cl$_2$ as eluent to afford Compound L as a black solid (1.36 g, 78%). The analytical data obtained from Compound L are listed below. M.p. 209° C. (DSC); IR (KBr) v 3024, 2921, 2221, 1587, 1542, 1286, 1107, 1071, 814 cm$^{-1}$; $^1$H NMR (CDCl$_3$, 400 MHz) δ 8.93 (s, 2H), 7.91 (d, J=4.4 Hz, 1H), 7.47 (s, 1H), 7.22-7.16 (m, 8H), 6.39 (d, J=4.4 Hz, 1H), 2.37 (s, 6H); $^{13}$C NMR (CDCl$_3$, 100 MHz) δ 164.5, 163.0, 158.2, 152.7, 143.3, 136.1, 135.1, 130.3, 126.6, 125.4, 119.8, 113.7, 112.9, 112.8, 80.1, 21.1; HRMS (m/z, FAB$^+$) Calcd. for C$_{26}$H$_{19}$N$_5$S 433.1361. found 433.1358.

Preparation of Other Compounds

In addition to the examples and embodiments shown above, to synthesize compounds containing an electron-donating moiety, a first electron-accepting moiety and a second electron-accepting moiety, a substituted or unsubstituted diphenylamine is first reacted with a substituted or unsubstituted brominated thiophene, furan, benzene, or thiazole using palladium acetate (Pd(OAc)$_2$) as the catalyst, to obtain a compound with an electron-donating moiety. After that, the resulting product is substituted by SnBu$_3$, followed by Stille coupling reaction with a brominated compound having a first electron-accepting moiety (e.g. benzoxadiazole or benzoselenadiazole) substituted by a second electron-accepting moiety (e.g. vinylene substituted by nitro group, ester group and/or cyano group).

Diphenylamine with benzene ring substituted by ether group of different carbon number can be prepared by the method disclosed in PCT Patent Publication No. 2009/141288 A2; diphenylamine with benzene ring substituted by amino group of different carbon number can be prepared by the method disclosed in J. Am. Chem. Soc. 2002, 124, 11085-11092.

Brominated thiophene substituted by alkyl or ether group of different carbon number can be prepared by the processes disclosed in Heterocycles 1997, 44, 75-80; Macromolecules 2011, 44, 2006-2015; Macromolecules 2010, 43, 8709-8710; Tetrahedron Letters 2010, 51, 4526-4529; and Macromolecules 2009, 42, 663-670. Brominated thiophene substituted by alkyl or ether group of different carbon number can be prepared by the processes similar to those disclosed above by a person skilled in the art.

Brominated 2,1,3-benzoxadiazole substituted by dicyanovinylene can be prepared by brominating 4-methylbenzoxadiazole, which is disclosed in China Patent No. 1847233, followed by the steps (i) to (iii) of Chemical Synthesis Scheme I shown above. Brominated 2,1,3-benzoselenadiazole substituted by dicyanovinylene can be prepared by brominating 4-methylbenzoselenadiazole, which is disclosed in PCT Publication No. 2009/034396 A2, followed by the steps (i) to (iii) of Chemical Synthesis Scheme I shown above. In addition, different Ar$_2$ as the first electron-accepting moiety can be prepared, as disclosed in Organic Process Research & Development 2003, 7, 318-323 and Tetrahedron Letters 2000, 41, 10299-10302, by reacting 2,3-diaminotoluene with diketone,

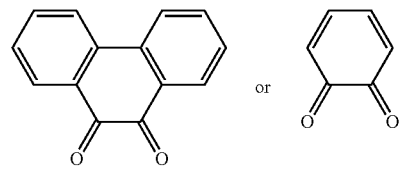 [SMILES: O=C1C(=O)c2ccccc2-c2ccccc21 ; O=C1C=CC=CC1=O]

which is unsubstituted or substituted by C$_1$-C$_6$ alkyl group, cyano group or phenyl group, followed by bromination and the steps (i) to (iii) of Chemical Synthesis Scheme I shown above.

In addition to dicyanovinylene, the second electron-accepting moiety may also be vinylene independently substituted by nitro group, ester group and/or cyano group, by using dinitromethane, nitroacetonitrile, cyano-substituted ester or the like in place of malononitrile in the step (iii) of Chemical Synthesis Scheme I shown above.

EXAMPLE

Fabrication and Testing of Solar Cells I

Compound D, purchased fullerene $C_{60}$ or $C_{70}$ and BCP were subject to purification by temperature-gradient sublimation before use. The organic and metal oxide (e.g. $MoO_3$) thin films and metal electrodes (e.g. silver) were deposited on indium tin oxide (ITO) coated glass substrates in a high vacuum chamber with base pressure $\sim 1 \times 10^{-6}$ Torr. The sheet resistance of ITO is about 150 $\Omega$/sq. The deposition was performed at rate of 2-3 Å with the substrate held at room temperature. Thicknesses were monitored using a crystal oscillator during deposition. The active area of the cells had an average size of 2.5-5 $mm^2$. Devices were encapsulated using a UV-cured sealant available from Everwide Chemical Co., Epowide EX and a cover glass under the dry nitrogen atmosphere after fabrication and were measured in air. Compound D was used to fabricate the devices summarized in Table I under different deposition conditions.

TABLE I

| Device No. | 1st Electrode | Hole transporting layer | PMHJ active layer | Electron transporting layer | 2nd Electrode |
|---|---|---|---|---|---|
| 1 | ITO | $MoO_3$ (30 nm) | compd D(3 nm)/ compd D:$C_{60}$(v/v 1:1, 40 nm)/$C_{60}$ (20 nm) | BCP (10 nm) | Ag (150 nm) |
| 2 | ITO | $MoO_3$ (30 nm) | compd D(5 nm)/ compd D:$C_{60}$(v/v 1:1, 40 nm)/$C_{60}$ (20 nm) | BCP (10 nm) | Ag (150 nm) |
| 3 | ITO | $MoO_3$ (30 nm) | compd D(7 nm)/ compd D:$C_{60}$(v/v 1:1, 40 nm)/$C_{60}$ (20 nm) | BCP (10 nm) | Ag (150 nm) |
| 4 | ITO | $MoO_3$ (30 nm) | compd D(9 nm)/ compd D:$C_{60}$(v/v 1:1, 40 nm)/$C_{60}$ (20 nm) | BCP (10 nm) | Ag (150 nm) |
| 5 | ITO | $MoO_3$ (5 nm) | compd D(7 nm)/ compd D:$C_{70}$(v/v 1:1, 40 nm)/$C_{70}$ (7 nm) | BCP (10 nm) | Ag (150 nm) |
| 6 | ITO | $MoO_3$ (10 nm) | compd D(7 nm)/ compd D:$C_{70}$(v/v 1:1, 40 nm)/$C_{70}$ (7 nm) | BCP (10 nm) | Ag (150 nm) |
| 7 | ITO | $MoO_3$ (20 nm) | compd D(7 nm)/ compd D:$C_{70}$(v/v 1:1, 40 nm)/$C_{70}$ (7 nm) | BCP (10 nm) | Ag (150 nm) |
| 8 | ITO | $MoO_3$ (30 nm) | compd D(7 nm)/ compd D:$C_{70}$(v/v 1:1, 40 nm)/$C_{70}$ (7 nm) | BCP (10 nm) | Ag (150 nm) |

Current density-voltage characteristics were measured with a SourceMeter Keithley 2636A under illumination of AM1.5G solar light from a xenon lamp solar simulator available from Abet Technologies. The incident light intensity was calibrated as 100 $mW/cm^2$. Photoelectric parameters for the devices are shown by Table II.

TABLE II

| Device No. | $V_{oc}$ (V) | $J_{sc}$ ($mA/cm^2$) | FF | $\eta_{PCE}$ (%) |
|---|---|---|---|---|
| 1 | 0.79 | 10.04 | 0.51 | 4.02 |
| 2 | 0.80 | 10.68 | 0.50 | 4.11 |
| 3 | 0.80 | 11.40 | 0.48 | 4.41 |
| 4 | 0.80 | 10.20 | 0.48 | 3.91 |
| 5 | 0.79 | 14.68 | 0.50 | 5.81 |
| 6 | 0.79 | 14.00 | 0.50 | 5.50 |
| 7 | 0.79 | 13.74 | 0.50 | 5.41 |
| 8 | 0.79 | 12.80 | 0.49 | 4.98 |

EXAMPLE

Fabrication and Testing of Solar Cells II

Similarly, Compounds E, F and G were fabricated into the solar cells shown in Table III and tested. The results are summarized in Table IV.

TABLE III

| Device No. | 1st Electrode | Hole transporting layer | PMHJ active layer | Electron transporting layer | 2nd Electrode |
|---|---|---|---|---|---|
| 9 | ITO | $MoO_3$ (30 nm) | compd E(7 nm)/ compd E:$C_{70}$(v/v 1:1, 40 nm)/$C_{70}$ (7 nm) | BCP (10 nm) | Ag (150 nm) |
| 10 | ITO | $MoO_3$ (5 nm) | compd F(7 nm)/ compd F:$C_{70}$(v/v 1:1, 40 nm)/$C_{70}$ (7 nm) | BCP (10 nm) | Ag (150 nm) |
| 11 | ITO | $MoO_3$ (5 nm) | compd G(7 nm)/ compd G:$C_{70}$(v/v 1:1, 40 nm)/$C_{70}$ (7 nm) | BCP (10 nm) | Ag (150 nm) |

TABLE IV

| Device No. | $V_{oc}$ (V) | $J_{sc}$ ($mA/cm^2$) | FF | $\eta_{PCE}$ (%) |
|---|---|---|---|---|
| 9 | 0.84 | 11.40 | 0.46 | 4.44 |
| 10 | 0.995 | 12.22 | 0.49 | 5.98 |
| 11 | 0.922 | 13.83 | 0.53 | 6.78 |

EXAMPLE

Fabrication and Testing of Solar Cells III

Compound L was fabricated into the solar cells shown in Table V and tested. The results are summarized in Table VI.

TABLE V

| Device No. | 1st Electrode | Hole transporting layer | PMHJ active layer | Electron transporting layer | 2nd Electrode |
|---|---|---|---|---|---|
| 12 | ITO | $MoO_3$ (20 nm) | compd L(5 nm)/ compd L:$C_{60}$(v/v 1:1, 30 nm)/$C_{60}$ (20 nm) | BCP (10 nm) | Ag (150 nm) |

TABLE V-continued

| Device No. | 1st Electrode | Hole transporting layer | PMHJ active layer | Electron transporting layer | 2nd Electrode |
|---|---|---|---|---|---|
| 13 | ITO | MoO$_3$ (20 nm) | compd L(5 nm)/ compd L:C$_{60}$(v/v 1:1, 40 nm)/C$_{60}$ (20 nm) | BCP (10 nm) | Ag (150 nm) |
| 14 | ITO | MoO$_3$ (20 nm) | compd L(7 nm)/ compd L:C$_{60}$(v/v 1:1, 40 nm)/C$_{60}$ (20 nm) | BCP (10 nm) | Ag (150 nm) |
| 15 | ITO | MoO$_3$ (20 nm) | compd L(9 nm)/ compd L:C$_{60}$(v/v 1:1, 40 nm)/C$_{60}$ (20 nm) | BCP (10 nm) | Ag (150 nm) |
| 16 | ITO | MoO$_3$ (20 nm) | compd L(7 nm)/ compd L:C$_{70}$(v/v 1:1, 40 nm)/C$_{70}$ (6 nm) | BCP (10 nm) | Ag (150 nm) |
| 17 | ITO | MoO$_3$ (20 nm) | compd L(7 nm)/ compd L:C$_{70}$(v/v 1:1, 40 nm)/C$_{70}$ (10 nm) | BCP (10 nm) | Ag (150 nm) |
| 18 | ITO | MoO$_3$ (20 nm) | compd L(7 nm)/ compd L:C$_{70}$(v/v 1:1, 40 nm)/C$_{70}$ (12 nm) | BCP (10 nm) | Ag (150 nm) |

TABLE VI

| Device No. | $V_{oc}$ (V) | $J_{sc}$ (mA/cm$^2$) | FF | $\eta_{PCE}$ (%) |
|---|---|---|---|---|
| 12 | 0.94 | 6.4 | 0.53 | 3.1 |
| 13 | 0.94 | 7.7 | 0.53 | 3.9 |
| 14 | 0.95 | 8.3 | 0.54 | 4.3 |
| 15 | 0.95 | 7.6 | 0.54 | 3.9 |
| 16 | 0.95 | 12.1 | 0.56 | 6.4 |
| 17 | 0.95 | 11.4 | 0.56 | 6.1 |
| 18 | 0.95 | 11.1 | 0.57 | 6.0 |

While the invention has been described in terms of what is presently considered to be the most practical and preferred embodiments, it is to be understood that the invention is illustrative and needs not to be limited to the above embodiments. On the contrary, it is intended to cover various modifications and similar arrangements included within the spirit and scope of the appended claims which are to be accorded with the broadest interpretation so as to encompass all such modifications and similar structures.

What is claimed is:

1. A compound represented by Formula (I)

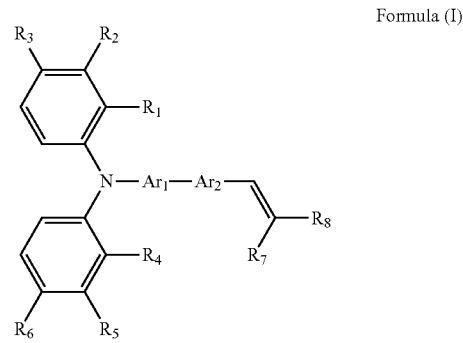

Formula (I)

wherein $R_1$ to $R_6$ are independently selected from H, $C_1$-$C_6$ alkyl group, $C_1$-$C_6$ ether group, and amino group substituted by $C_1$-$C_6$ alkyl group;

$Ar_1$ is selected from

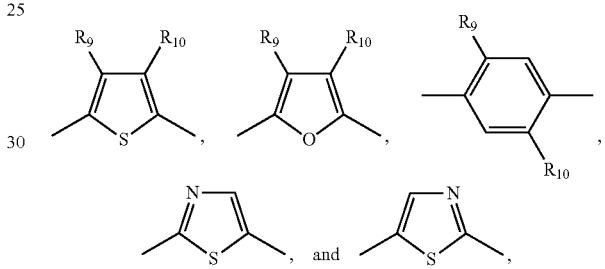

wherein $R_9$ and $R_{10}$ are independently selected from H, F, $C_1$-$C_6$ alkyl group, and $C_1$-$C_6$ ether group;

$Ar_2$ is selected from

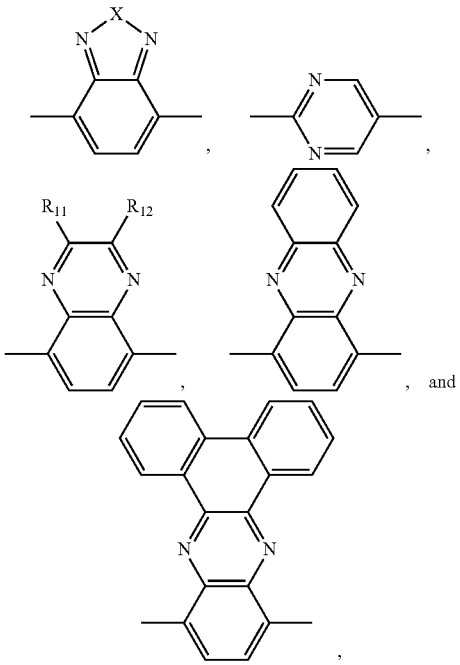

wherein X is O, S, or

Se, and $R_{11}$ and $R_{12}$ are independently selected from H, $C_1$-$C_6$ alkyl group, cyano group, and phenyl group; and $R_7$ and $R_8$ are independently selected from cyano group, nitro group, and $C_1$-$C_8$ ester group of carboxylic acid.

2. The compound of claim 1, wherein $R_1$ to $R_6$ are independently selected from H and $C_1$-$C_6$ alkyl group; $Ar_1$ is selected from

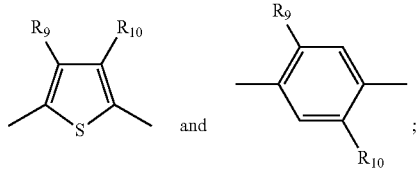

$Ar_2$ is selected from

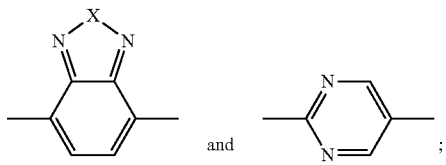

and $R_7$ and $R_8$ are both cyano group.

3. The compound of claim 2, wherein X is S.

4. The compound of claim 2, wherein $R_9$ and $R_{10}$ are independently selected from H and F.

5. The compound of claim 1, wherein $R_1$, $R_2$, $R_4$ and $R_5$ are H, and $R_3$ and $R_6$ are $C_1$-$C_6$ alkyl group.

6. The compound of claim 5, wherein $Ar_1$ is selected from

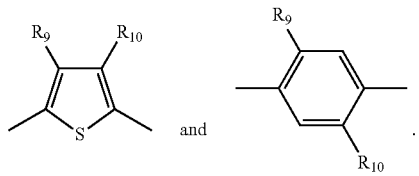

7. The compound of claim 6, wherein $R_9$ and $R_{10}$ are independently selected from H and F.

8. An organic thin-film solar cell comprising a first electrode, a hole transporting layer, an active layer, an electron transporting layer and a second electrode which are sequentially stacked, wherein the active layer comprises a compound represented by Formula (I)

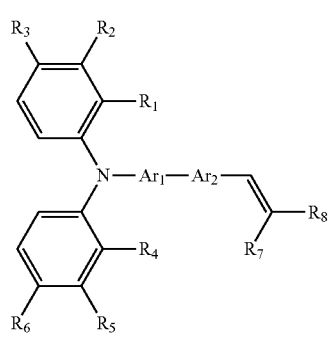

Formula (I)

wherein $R_1$ to $R_6$ are independently selected from H, $C_1$-$C_6$ alkyl group, $C_1$-$C_6$ ether group, and amino group substituted by $C_1$-$C_6$ alkyl group;

$Ar_1$ is selected from

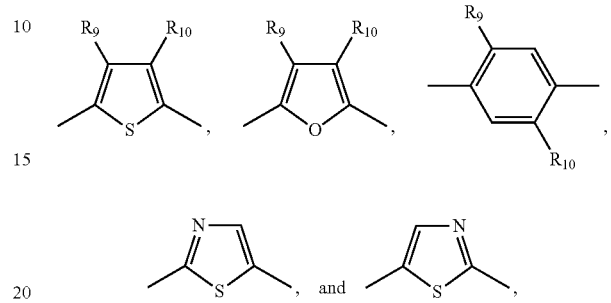

wherein $R_9$ and $R_{10}$ are independently selected from H, F, $C_1$-$C_6$ alkyl group, and $C_1$-$C_6$ ether group;

$Ar_2$ is selected from

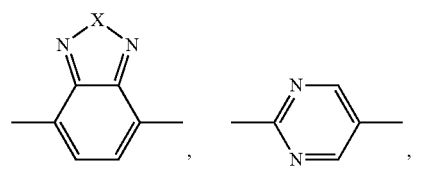

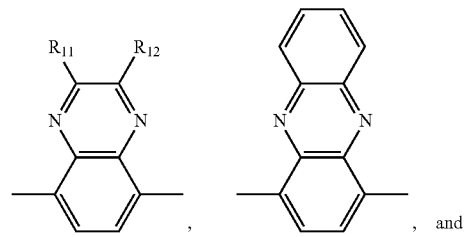

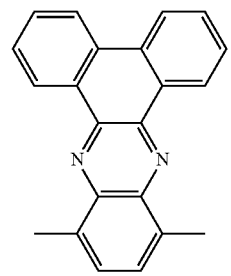

wherein X is O, S, or

Se, and $R_{11}$ and $R_{12}$ are independently selected from H, $C_1$-$C_6$ alkyl group, cyano group, and phenyl group; and $R_7$ and $R_8$ are independently selected from cyano group, nitro group, and $C_1$-$C_8$ ester group of carboxylic acid.

9. The organic thin-film solar cell of claim 8, wherein $R_1$, $R_2$, $R_4$ and $R_5$ are H;

$R_3$ and $R_6$ are $C_1$-$C_6$ alkyl group;

Ar₁ is selected from
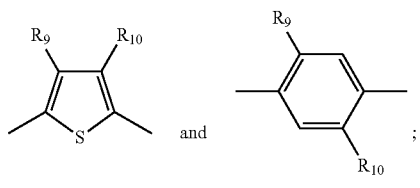
and ;
Ar₂ is selected from
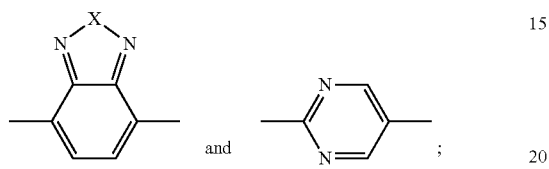
and ;
and
R₇ and R₈ are both cyano group.
10. The organic thin-film solar cell of claim 9, wherein X is S, and R₉ and R₁₀ are independently selected from H and F.
* * * * *